United States Patent
Porter

(10) Patent No.: US 7,687,053 B2
(45) Date of Patent: Mar. 30, 2010

(54) EMBOLIC COMPOSITIONS WITH NON-CYANOACRYLATE RHEOLOGY MODIFYING AGENTS

(75) Inventor: Stephen C. Porter, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1067 days.

(21) Appl. No.: 09/933,316

(22) Filed: Aug. 20, 2001

(65) Prior Publication Data

US 2003/0039696 A1    Feb. 27, 2003

(51) Int. Cl.
*A61K 49/04* (2006.01)

(52) U.S. Cl. .................................. 424/9.411

(58) Field of Classification Search ........... 424/9.4, 424/9.411, 9.45, 422, 601, 604, 605, 644, 424/649; 514/522, 526, 153, 150, 154; 604/506, 604/508, 518
See application file for complete search history.

(56) References Cited

U.S. PATENT DOCUMENTS

| | | | |
|---|---|---|---|
| 3,264,249 A | 8/1966 | Araki et al. | |
| 3,728,375 A | 4/1973 | Coover, Jr. et al. | 260/465.4 |
| 4,713,235 A | 12/1987 | Krall | |
| 4,997,861 A | 3/1991 | Hechenberger et al. | |
| 5,322,499 A | 6/1994 | Liprie | 600/8 |
| 5,447,710 A * | 9/1995 | Na et al. | 424/9 |
| 5,702,361 A | 12/1997 | Evans et al. | 604/53 |
| 5,713,917 A | 2/1998 | Leonhardt et al. | 606/194 |
| 5,739,205 A | 4/1998 | Nishino et al. | |
| 5,795,331 A | 8/1998 | Cragg et al. | 604/96 |
| 5,817,343 A | 10/1998 | Burke | 424/489 |
| 5,882,334 A | 3/1999 | Sepetka et al. | 604/96 |
| 5,925,683 A | 7/1999 | Park | 514/772.1 |
| 6,015,424 A | 1/2000 | Rosenbluth et al. | 606/200 |
| 6,015,541 A | 1/2000 | Greff et al. | 424/1.25 |
| 6,020,004 A | 2/2000 | Shah | 424/501 |
| 6,037,366 A | 3/2000 | Krall et al. | 514/527 |
| 6,068,857 A | 5/2000 | Weitschies et al. | 424/489 |
| 6,160,025 A * | 12/2000 | Slaikeu et al. | 514/772.1 |
| 6,203,779 B1 * | 3/2001 | Ricci et al. | 424/9.45 |
| 6,476,069 B2 * | 11/2002 | Krall et al. | 514/527 |
| 6,476,070 B2 * | 11/2002 | Krall et al. | 514/527 |
| 6,538,026 B1 * | 3/2003 | Krall et al. | 514/527 |
| 2002/0018752 A1 | 2/2002 | Krall et al. | |

FOREIGN PATENT DOCUMENTS

| | | |
|---|---|---|
| EP | 0 050 457 A1 | 10/1981 |
| EP | 0 323 720 A1 | 12/1988 |
| EP | 0 686 681 A1 | 5/1995 |
| WO | WO 00/44287 | 8/2000 |
| WO | WO 01/89501 A1 | 11/2001 |

OTHER PUBLICATIONS

PCT International Search Reaort dated Oct. 21, 2002.
U.S. Appl. No. 60/058,510, filed Sep. 11, 1997.
U.S. Appl. No. 09/823,775, filed Sep. 11, 1998.
Siskin et al. "Pathologic Findings in A Uterine Leiomyoma After Bilateral Uterine Artery Embolization", *JVIR* 10:891-894, (1999).

* cited by examiner

*Primary Examiner*—Yong S Chong
(74) *Attorney, Agent, or Firm*—Mayer & Williams P.C.; David B. Bonham; Keum J. Park

(57) ABSTRACT

Compositions for embolization are disclosed herein. The compositions disclosed can have a matrix-forming component, a solid-aggregate material, and a rheology modifying agent, wherein the matrix-forming component includes at least alkyl cyanoacrylate monomers, a stabilizer, and a plasticizer, and the solid-aggregate material includes at least a radiopacifier. The composition and a method of administering the composition are useful for treating vasculature abnormalities, particularly when the composition solidifies upon contact with an ionic environment, such as blood.

24 Claims, No Drawings

EMBOLIC COMPOSITIONS WITH NON-CYANOACRYLATE RHEOLOGY MODIFYING AGENTS

FIELD OF THE INVENTION

The present invention relates generally to polymer compositions, and more particularly, liquid polymer compositions capable of forming a solid embolic block upon administration in an ionic environment, such as blood. The composition can be used for treating vascular abnormalities, including brain aneurysms. In particular, the compositions of the present invention comprise a matrix-forming component and a solid-aggregate material, which can combine to form an embolic composition upon administration.

BACKGROUND OF THE INVENTION

Vascular embolization often is the chosen method for controlling bleeding in the blood vessels or occluding blood supply to solid mass tumors or vascular aneurysms. Currently available therapeutic regimens for treating solid mass tumors can be difficult to administer, particularly depending on the properties of the embolic, or bulking, composition used. Aneurysms, arteriovenous malformations ("AVMs") and other vascular abnormalities, for example, vascular tumors, can be difficult to treat. Treatment of lesions and growths that occur in the brain or brain stem is especially complicated due to the particularly sensitive nature of the surrounding tissue.

Cyanoacrylate adhesives have been used for treatment of AVMs and other vascular abnormalities for almost thirty years. The usefulness of these compositions has been limited by cytotoxicity and the amount of heat generated by polymerization. Recent developments in the formulation of cyanoacrylate compositions have improved the usefulness of such compositions in treating vascular disease. For example, U.S. Pat. No. 6,015,541, issued Jan. 18, 2000, describes a radioactive composition for treating solid mass tumors comprising a biocompatible free polymer, a biocompatible solvent, and about 0.1 to about 25 weight percent of a water in soluble radioisotope. The biocompatible polymer can be a cyanoacrylate free polymer variant and the composition contains n-butyl-2-cyanoacrylate (NBCA) in combination with an iridium isotope. Although such a composition was demonstrated to have effect on a solid mass tumor in a rabbit, the viscosity and suspension properties of the composition were less than desirable. Another disadvantage is that the iridium isotope settled within several seconds after mixing, requiring constant, gentle agitation to prepare a prolonged suspension.

A composition including 2-hexyl cyanoacrylate and gold was described in U.S. Pat. No. 6,037,366, issued Mar. 14, 2000. The cyanoacrylate composition demonstrated improved cohesion properties compared to previous compositions. Administration of such compositions involved mixing two separate components of material immediately prior to administration into the AVM. One component contained cyanoacrylate liquid monomer containing pure phosphoric acid hydroquinone and p-methoxyphenol. The second component contained pure powdered gold, a small amount of pre-polymerized cyanoacrylate polymer and a fatty acid, ethyl myristate. The improved cohesion properties kept the materials together during the time required for polymerization. Although incorporation of a small amount of pre-polymerized cyanoacrylate monomer is mentioned in the composition, there is no mention of any non-cyanoacrylate rheology or viscosity modifying agent.

Alkyl cyanoacrylate compositions in general were described in International PCT publication WO 00/44287, published on Aug. 3, 2000. The compositions contained the alkyl cyanoacrylate and at least one inhibitor, and a second component comprised of a resultant aggregate structure formed from an alkyl cyanoacrylate monomer, an alkyl esterified fatty acid and an opacificant agent. The composition formed the resultant aggregate structure upon contact with blood. Although these compositions demonstrate improved properties over prior compositions, inadvertent tissue adhesion to microcatheter delivery devices used to administer such compositions remains a problem. There is no suggestion or recognition that such properties can be improved by a non-cyanoacrylate rheology modifying agent.

Accordingly, there remains a need for an improved composition for treating vascular abnormalities, such as AVMs or brain aneurysms. The improved composition would have properties of apparent viscosity between 25 cP and 2000 cP, improved cohesiveness, improved suspension of dense radiopacifier powders, and radiopacity. In addition, the composition would form a solid composition possessing improved hydrolytic stability upon contact with an aqueous environment, for example, blood.

SUMMARY OF THE INVENTION

The invention relates to a composition comprising a matrix-forming component and optionally a solid-aggregate material. The matrix-forming component can comprise liquid alkyl cyanoacrylate monomers and at least a stabilizer and a plasticizer. The composition can incorporate a solid-aggregate material with the matrix-forming component, which typically consists of at least a radiopaque powder, i.e. a radiopacifier. A rheology modifying agent also can be incorporated into the composition, either in combination with the matrix-forming component or with the solid-aggregate material. The rheology modifying agent can be a non-cyanoacrylate polymer or a fine inorganic particulate compound, other than the radiopacifier.

The composition is useful in a therapeutic regimen for treating vascular abnormalities. Vascular abnormalities that can be treated by administration of the composition include, for example, AVMs, aneurysms, fistulas, and tumors. Upon contact with an ionic environment, the liquid composition rapidly increases in viscosity, forming a solidified composition having the consistency of a rubbery polymeric matrix.

The method of the invention includes administering the composition for tissue bulking, filling, or occluding, either partially or entirely, a volume or cavity in a mass. Typically, the volume or cavity filled by the method of the present invention is a lumen or passageway in the body, for example, a blood vessel, a duct, an aneurysm, or a fistula. The solid composition formed in the method of the invention is useful for abating disease of the vascular tissues or by cutting off the blood supply to undesired tissue. A tumor or abnormality is occluded by cutting off the blood supply to the diseased area, resulting in diminished growth or death of the tumor or abnormality.

The method of the invention also includes administering the composition to embolize a vascular space. The composition is administered to a patient, typically in need of treatment for vascular abnormalities, to form an embolic block at the site of diseased, damaged, or otherwise compromised vasculature.

The above and other aspects, advantages, and novel features of the invention will become apparent from the following detailed description of the invention.

DETAILED DESCRIPTION OF THE PREFERRED EMBODIMENTS

Therefore, in one aspect, the invention relates to matrix-forming components comprising an alkyl cyanoacrylate monomer in combination with at least a stabilizer and a plasticizer. The matrix-forming components also can include a polymeric rheology modifying agent. The matrix-forming components can be used with one or more solid-aggregate materials. All the materials used are either incorporated into a single injectable embolic composition along with the matrix-forming components or can be included in one of a number of separately packaged mixtures that are combined prior to use to form the embolic composition. The stabilizing component is comprised of an acidic stabilizer, a free radical inhibitor, an antioxidant, or a mixture thereof. The plasticizer can be selected from a group of polymeric or non-polymeric compounds that impart flexibility, prevent brittleness, reduce adhesiveness to catheter delivery devices, and are compatible with alkyl cyanoacrylate monomers. The solid-aggregate material comprises a radiopacifier, and also can include a rheology modifying agent.

The rheology modifying agent is a non-cyanoacrylate polymer or fine solid particulate compound that is not radiopaque. The rheology modifying agent is capable of increasing the Newtonian viscosity of the composition and/or capable of imparting non-Newtonian behavior upon the liquid composition, such that it demonstrates thixotropic, pseudo-plastic, or plastic fluid behavior. Fluids that exhibit such behaviors generally can be classified as "shear thinning."

The rheology modifying agent can impart properties on the liquid injectable composition of an apparent viscosity of between 25 cP and 2000 cP, and preferably between about 100 cP and about 300 cP, improved cohesiveness over cyanoacrylate-polymerizing compositions, improved suspension and stability of dense radiopacifying powders, and additional radiopacity. The rheology modifying agent may also impart an improved surface tension of the composition as it solidifies.

In this aspect of the invention, the rheology modifying agent is optionally incorporated into the matrix-forming component or the solid-aggregate material, provided that the composition contains at least one rheology modifying agent. The composition is rendered radiopaque by including the radiopacifier, which typically comprises a fine powder or submicron sized particles having a radiopaque nature. Typically, the radiopacifer component has high x-ray absorbance, either alone, or in combination, with iodinated oils.

The composition can also be useful for bulking muscular tissues. Tissues that can be treated include smooth muscle sphincters and other tissues that can benefit from volumetric augmentation. The composition is particularly useful when a radiopacifier is incorporated in the composition for visualization of the administration of the composition.

In another aspect, the method of the invention relates to embolizing a vascular space, or cavity, by administering the composition of the invention. The method can be accomplished by combining the matrix-forming components of the invention with one or more solid-aggregate materials. In particular, the matrix-forming components, including at least liquid cyanoacrylate monomers, a stabilizer, and a plasticizer, are exposed to a solid-aggregate material that comprises at least a radiopacifier. The composition is typically a liquid injectable composition that solidifies upon contact with an ionic environment, for example, blood. Either the matrix-forming component or the solid-aggregate material contains a non-cyanoacrylate compound, which imparts improved rheology, cohesiveness, suspension stability, and radiopacity properties of the liquid injectable composition. In addition, the inclusion of a non-cyanoacrylate polymer compound can impart an improved hydrolytic stability on the solidified composition rendered in the body.

In another aspect, the method of the invention is useful for stabilizing or mitigating rupture of an aneurysm. The composition of the invention can be used to occlude the interior space of an unruptured or previously ruptured aneurysm. Methods of non-surgical treatment using non-alkyl cyanoacrylate compositions are described in *J. Vascular and Intervention Radiology*, 10:891-894, July-August 1999.

The composition is delivered by any suitable device for administering a liquid composition. One example of a suitable device presently available is a microcatheter, such as the EXCELSIOR™ microcatheter (Target Therapeutics, Inc., Fremont, Calif., U.S.A.). The invention also can employ any method using any number of commercially available devices, for example, catheters, catheter coils, catheter wires, stents, or catheter balloons. An example of a commercially available device suitable for augmenting the delivery of the composition is the SENTRY™ Occlusion Balloon System, available from Target Therapeutics, Inc., Fremont, Calif., U.S.A. The method can be used in combination with affixing therapeutics, chemotherapeutics, radiation delivery devices, and gene therapy compositions, which are delivered to the desired location in proximity with the composition of the invention.

As used herein, the terms "adhesion" or "adhesive" mean the characteristic or tendency of a material to be attracted to the surface of a second material. Adhesion occurs as the result of interactions between two materials. Depending on the characteristics of the second material relative to the first material, adhesion may or may not occur. For a single material, e.g. the composition of the present invention, the presence of adhesion is demonstrated by a material sticking to the wall of a lumen of a blood vessel, i.e. there is adhesion between the material and the lumen wall. Conversely, the absence of adhesion is demonstrated for the same material where a microcatheter tip used to deposit the material can be removed from the material, i.e., there is little adhesion between the material and microcatheter tip.

As used herein, the term "alkyl" refers to a carbon chain of one to eighteen atoms, where the carbon atoms can be linear or branched.

As used herein, the term "ionic environment" refers to an environment that contains ions. The term "non-ionic" refers to an environment that is devoid of charged ions, or where the charged ions are complexed with other molecules, which effectively neutralize their charge. For example, a solution of water and a sugar, such as dextrose, and blood is an ionic environment.

As used herein, the term "lower-alkyl" refers to a carbon chain of one to eight carbon atoms where the carbon atoms can be linear or branched. Examples of lower-alkyl moieties include, but are not limited to, methyl, ethyl, n-butyl, isobutyl, pentyl, n-hexyl, 2-hexyl, n-heptyl, 2-heptyl, n-octyl, and 2-octyl.

As used herein, the term "branched alkyl" refers to a carbon chain of one to eighteen carbon atoms where the carbon chain contains at least one secondary or tertiary substituted carbon atom, for example, 2-hexyl, isobutyl, 2-heptyl, 2-octyl, and the like.

As used herein, the term "cohesion" or "cohesive" means the characteristic or tendency of a material to stick together to itself. For example, this characteristic is demonstrated by a material or composition remaining intact as a single mass when introduced into a stationary fluid, or a fluid stream in motion, such as blood. Lack of cohesive integrity results in the composition breaking up into multiple smaller subunits.

As used herein, the term "matrix-forming component" refers to the assemblage of one or more compounds, and preferably not more than 5 or 6 compounds, incorporated into the continuous phase of a solidified embolic composition.

As used herein, the term "solid-aggregate material" refers to one or more solid particulate compounds or matter, and preferably not more than 1 or 2 compounds, that are separate from, but generally dispersed within, the matrix of a solidified embolic composition.

The term "bulking agent" as used herein refers to a non-naturally occurring composition introduced into muscular, connective, or fatty tissues for the purpose of increasing the volume of such tissues.

As used herein, the term "embolic agent" refers to a non-naturally occurring composition introduced into a body cavity or the lumen of a blood vessel, duct, fistula, aneurysm, or other like body passageways for the purpose of forming an embolic composition.

The term "embolic composition" as used herein refers to the assemblage of the matrix-forming components and the solid-aggregate materials.

As used herein, the term "embolic block" or "embolic blockage" or occlusion refers to the end result from the administration of a composition useful as an embolic agent. The resulting embolic block mechanically blocks, totally or partially, the lumen of a blood vessel, duct, fistula or other like body passageways or, in a like manner, forms an occlusion within a cavity, such as an aneurysm.

As used herein, the term "alkyl cyanoacrylate monomer" refers to the chemical entity of the general structure $H_2C=C(CN)-C(O)O-R$, where R is an alkyl moiety of pone to eighteen carbon atoms, linear or branched, saturated or unsaturated, having the physical characteristic of being able to form the corresponding alkyl cyanoacrylate polymer. As used in the singular form, "alkyl cyanoacrylate monomer" also is intended to refer to more than one monomer, as would be understood by one with skill in the art.

As used herein, the term "alkyl cyanoacrylate polymer" means an oligomer or polymer resulting from the polymerization of an alkyl cyanoacrylate monomer.

As used herein, the term "radiopacifer" is a compound or composition that selectively absorbs or deflects radiation making the material visible under x-ray, or any like imaging technique. Typically, such agents include iodinated oils and brominated oils, and mixtures thereof, as well as commercially available compositions, such as PANTOPAQUE®, LIPIODOL® (Laboratories Guerbet, Aulnay-sous-Bois, France), and ETHIODOL® (Savage Laboratories, Melville, Md., U.S.A.). These commercially available materials render the composition radiopaque and also can dilute the amount of a liquid monomer thereby slowing the rate of polymerization. In addition, certain metals such as gold, platinum, tantalum, titanium, tungsten, barium sulfate, and the like, and mixtures thereof, have properties enabling them to act as radiopacifiers.

As used herein, the term "polymerization" refers to the chemical process where identical monomer units react chemically to form larger molecules comprised of said monomeric units as oligomers or polymers.

As used herein, the term "stabilizer" or "stabilizing component" means a compound or composition that can stop or slow down the rate of polymerization. Examples of such agents are phosphoric acid and hydroquinone.

As used herein, the term "vascular space" or "cavity" refers to an unfilled volume or hollow void in a mass. Examples of such cavities include, but are not limited by the following, as existing space within a mass, such as the lumen of a blood vessel, the sac of an aneurysm, a space created by a transiently placed external device, such as a catheter, needle, canula, or like device, a space created by a procedure, such as an excision or like procedure, a physical void created by implantation of an object, such as a stent or like device, or a void created by the composition.

As used herein, the term "stability" refers to the ability of a monomer component to resist degradation or polymerization after preparation but prior to use.

The alkyl cyanoacrylate monomers of the present invention are already known. The monomers can be prepared by forming the desired precursor ester, the corresponding alcohol and cyanoacetic acid. The reaction of the alkyl alcohol with the cyanoacetic acid forms an alkyl cyanoacetate, which can be converted into the desired alkyl cyanoacrylate compound. The preparation of the alkyl cyanoacrylate compounds has been described in U.S. Pat. No. 6,015,541, issued Jan. 18, 2000, U.S. Pat. No. 6,037,366, issued Mar. 14, 2000, and PCT International Publication WO 00/44287, published Aug. 3, 2000. Starting materials for preparing the alkyl cyanoacrylate monomer are commercially available from, for example, Aldrich Chemical Company, Sigma Chemical Company, or Fluka Chemical Company, or can be prepared by the procedures known to those with skill in the art.

Briefly, an alkyl alcohol, containing from 1 to 18 carbons, is reacted with cyanoacetic acid. The alcohol can contain from 1 to 18 carbons, for example, methyl, ethyl, propyl, butyl, pentyl, hexyl, heptyl, octyl, nonyl, deca, undeca, dodeca, trideca, tetradeca, pentadeca, hexadeca, and octadeca, and the like. Particularly advantageous alcohols are described in U.S. Pat. No. 3,728,375 entitled "Cyanoacrylate Adhesive Compositions", which is herein incorporated by reference in its entirety. Especially preferred alcohols are n-butyl, isobutyl, and 2-hexyl alcohols. About one molar equivalent of the alkyl alcohol is reacted with one mole of cyanoacetic acid in an organic solvent. A catalytic amount of p-tolulene sulfonic acid is added and the mixture is stirred and heated to reflux to afford the desired alkyl cyanoacetate.

The alkyl cyanoacetate undergoes Knoevenagel-type reaction to provide the alkyl cyanoacrylate. About one molar equivalent of the formaldehyde is dissolved in solvent, such as an organic alcohol, for example, methanol. The formaldehyde solution is reacted with about one molar equivalent of alkyl cyanoacetate in a dropwise manner, with stirring, to yield the desired alkyl cyanoacetate polymer. The reaction system is treated with trace amounts of the sulfur dioxide and the received flasks are treated with hydroquinone and 85% phosphoric acid to prevent polymerization of the monomers. After initial purification, the desired alkyl cyanoacrylate can be further purified using multiple distillation or other purification techniques known to those in the art, such as vacuum distillation, spinning band column, and the like. The preferred alkyl cyanoacrylate monomers comprise at least 4 carbon atoms. More preferred cyanoacrylate compounds comprise alkyl groups having from 4 to 10 carbon chains, for example, methyl, ethyl, propyl, butyl, pentyl, hexyl, heptyl, octyl, nonyl, deca, and the like. Especially preferred for the invention are alkyl cyanoacrylates containing from 4 to 8 carbons, for example, n-butyl, isobutyl, pentyl, 2-hexyl, 2-octyl, and the like. The preferred amount of cyanoacrylate monomer is about 20% to about 75%, by weight of the matrix-forming components. More preferably, the cyanoacrylate monomer comprises about 30% to about 70%, by weight of the matrix-forming components.

The alkyl cyanoacrylate monomer can be combined with a stabilizing component. The stabilizing component can comprise an acidic stabilizer, a free radical inhibitor, an antioxidant, or a mixture thereof. The acidic stabilizer can comprise at least one inorganic or organic acid. Examples of suitable inorganic acids include, but are not limited to, metallic acids, for example, phosphoric acid. Organic acids can include, but are not limited to, alkyl carboxylic acid, such as ethanoic acid, propanoic acid, butanoic acid, pentanoic acid, hexanoic acid, and the like, wherein the alkyl moiety ranges from 1 carbon, for example, acetic acid, through about 16 to 18 carbon atoms, for example, palmitic and stearic acid, respectively.

The free radical inhibitors commonly are low molecular weight electron acceptors. Examples of compounds that can inhibit free radicals in the composition include, but are not limited to, p-methoxyphenol, hydroquinone, glyoxides, and the like.

Antioxidants can reduce or inhibit the loss of electrons in the composition. Examples of antioxidants can include, but are not limited to, vitamins A, C, and E, for example carotenoids, ascorbic acid, and alpha-, beta-, delta-, and gamma-tocopherols, acetates and esters thereof, and the like, or mixtures thereof.

The acidic stabilizer, free radical inhibitor, antioxidant, or mixture thereof, can be used to inhibit anionic polymerization and the rate of such polymerization in the compound of the invention. The amount of stabilizer used in the composition is determined relative to the amount of alkyl cyanoacrylate, typically in terms of parts per million. For example, hydroquinone can be included in the composition in a range of about 50 to 100 parts per million (ppm). Phosphoric acid typically can be included in the composition of about 125 ppm to about 375 ppm. The amount of stabilizing component including the acid stabilizer and/or the free radical inhibitor, typically will be determined by one with skill in the art according to the components in the composition. Typically, the stabilizing component will comprise from about 50 to 500 ppm of the composition relative to the alkyl cyanoacrylate monomer. The alkyl cyanoacrylate monomer and stabilizing component can be packaged or delivered together, or as separate mixtures, with the solid-aggregate material.

The rheology modifying agent of the invention can be a non-cyanoacrylate polymer. The non-cyanoacrylate polymer is typically pre-polymerized and dissolved in the alkyl cyanoacrylate liquid monomers or, more preferably, dissolved in a plasticizer of the invention. The non-cyanoacrylate polymer is typically a polymer or copolymer compatible with the alkyl cyanoacrylate monomers. The non-cyanoacrylate polymer may be selected from the group of poly(acrylates), poly(alkenes), poly(alkyl oxides), poly(amides), poly(carbonates), cellulosic polymers and copolymers, poly(dienes), poly(esters), poly(methacrylates), poly(saccharides), poly(siloxanes), poly(styrenes), poly(urethanes), poly(vinyl ethers), poly(vinyl esters), polymers and copolymers having high iodine content, and other rubbery polymers compatible with alkyl cyanoacrylate monomers, or mixtures thereof, particularly those that impart the desired properties on the liquid injectable and solidified composition.

One with skill in the art will be able to determine the amount of polymer to be included in the composition based on the relative weight of the polymer and the desired viscosity of the liquid composition. Typically, the polymers will have molecular weight of above 75,000. More preferably, the polymer will have a molecular weight of greater than 200,000. The polymer can be included in a liquid medium, which can comprise either a plasticizer solution or the alkyl cyanoacrylate monomer itself.

The rheology modifying agent also can be a fine, inorganic particulate material. The rheology modifying agent is different from the radiopacifier and alters the Theological and cohesive properties of the embolic composition. The inorganic particulate material is typically incorporated with both the radiopacifier and the plasticizer. The inorganic particulate material may be selected from the group consisting of fumed silica, silicatious earths, for example bentonite, or other inorganic particulate gelling or suspending materials capable of altering the rheology of the embolic composition to possess properties of a thixotropic, pseudo-plastic, or plastic fluid. The size and concentration of the rheology modifying agent can be selected from a broad range of such suitable particulate materials provided that the particulate materials impart a thixotropic nature to the embolic composition. Suitable materials can include, for example, fumed silica particles of about 10 nanometers (0.1 micron) in diameter, and generally can comprise particles of less than about 5 microns in diameter, depending on the nature of the particle selected.

An embolizing composition including an inorganic particulate rheology modifying agent will exhibit a change in apparent viscosity upon moving from an environment with a first hydrodynamic shear rate to an environment having a second hydrodynamic shear rate. The effect sought is typically referred to as "shear thinning behavior." For example, the embolizing composition has a low apparent viscosity when flowing through a microcatheter and a relatively high apparent viscosity when it exits the microcatheter and is no longer flowing. This change in viscosity is not associated with the polymerization of the alkyl cyanoacrylate monomer, but is a property of the fluid embolizing composition in absence of any chemical reaction.

A rheology modifying agent can impart properties of the liquid injectable composition, such as improved viscosity, improved cohesiveness, improved suspension, stability of dense radiopacifying powders, and additional radiopacity. A solidified composition including a polymeric rheology modifying agent can have properties demonstrating improved hydrolytic stability when compared to cyanoacrylate compositions containing pre-polymerized cyanoacrylate.

A polymeric rheology modifying agent preferably comprises from about 0% to about 10%, by weight of the matrix-forming components. More preferred amounts of the rheology modifying agents are from about 1% to about 5%, by weight of the matrix-forming components.

An inorganic particulate rheology modifying agent would preferably comprise from about 0% to about 75%, by volume of the solid-aggregate material. More preferably, the inorganic particulate rheology modifying agent comprises from about 0% to about 40%, by volume of the solid-aggregate material. The polymeric or inorganic particulate rheology modifying agents can be used in the embolic composition independently or in combination with one another.

The matrix-forming components include a plasticizer. The plasticizer imparts flexibility to the solidified composition and prevents brittleness of the solidified polymer. The plasticizer can be a low molecular weight organic molecule, for example an organic ester, or a low molecular weight polymer. Suitable organic esters typically contain 10 or more carbon atoms. Preferably, the organic esters contain from about 10 to about 18 carbon atoms. Suitable polymeric plasticizers typically demonstrate a glass transition temperature below room temperature, for example, less than 20° C. The desired plasticizer is compatible with the alkyl cyanoacrylate monomer and can impart properties such as flexibility, elasticity, and minimal catheter adhesivity, to the solidified composition. Examples of plasticizers suitable for the invention include, but are not limited to, aromatic esters, alkyl esters, phthalate esters, citrate esters, glycerol esters, plant derived oils, animal derived oils, silicone oils, iodonated oils, vitamins A, C, E, and acetates and esters thereof, and other biocompatible plasticizers, and the like, or mixtures thereof. Where the plasticizer is an iodinated oil, the plasticizer can be incorporated into the composition to enhance the radiopacity of the composition.

The plasticizer typically comprises about 10% to about 75%, by weight of the matrix-forming components. Preferably, the plasticizer comprises 30% to about 60%, by weight of the matrix-forming components.

The composition also can be rendered radiopaque by the inclusion of a separate radiopacifier, a compound for imparting x-ray absorbing or scattering properties to the composition. The radiopacifier comprises fine or sub-micron sized particles demonstrating high x-ray absorbance, either alone or in combination, with other components. The amount and size of the particles can be determined by one with skill in the art in the manner that is suitable for fluoroscopic visualization of the embolic material during injection through a suitable device, such as a microcatheter, and for achieving the desired stability of the suspended particulates. More particularly, the radiopacifier will comprise a compound, wherein the particle size is typically less than one micron. The preferred particle size of a suitable radiopacifier is from about 50 to about 500 nanometers in diameter.

Examples of compounds suitable for the radiopacifier component are tantalum (Ta), tantalum oxide (TaO), gold (Au), platinum (Pt), zirconium (Zr), zirconium oxide (ZrO), bismuth subcarbonate, and barium sulfate. The materials can be used in combination with iodinated oils or with a iodinated polymeric component or an iodinated plasticizer.

The radio-opaque particles and/or inorganic rheology modifying particles can be treated in a manner consistent with improving their colloidal, or suspension, stability. Stabilized suspensions maintain homogeneous properties and can thereby reduce the incidence of encountering differential flow properties and/or differential radiopacity of the embolic liquid prior to and during the process of injection. The particles can be pre-treated with the addition of chemical agents, which can either modify the surface chemistry of the particles by molecular adsorption or via a chemical reaction. The surface-modifying molecules are typically adsorbed to or bonded to the surface of the particle, improving the stability of a suspension of the particles within the composition. The chemical pre-treatment of the particles typically changes the effective diameter of the particles or reduces particle-particle interactions by (1) increasing steric repulsion, (2) decreasing electrostatic attractions, (3) changing the surface energy of the particles, or (4) adding or removing potential reactive sites on the surface of the particles. The modifications generally are accomplished by reactive coupling of long-chain molecules, for example $C_6$-polymers, to the particles, such as silane coupling to TaO or thiol coupling to Au; addition of a surfactant to the formulation, and preferably a non-ionic surfactant; addition of an ionic molecular species to the formulation, including for example species from simple salts to ionic polymers; or the addition of any species that will adsorb to the particles or influence electrostatic forces between particles as known to those of skill in the art.

The solid-aggregate portion of the material is preferably stored separately from the monomer. A hydrophobic carrier liquid may be used, for example, the plasticizer, an oil-based contrast agent, or other hydrophobic low molecular weight biocompatible additives. The amount of radiopacifier incorporated into the composition is about 5 to about 40 volume percent based on the volume of the embolic composition. More preferably, the amount of radiopacifier is from about 8 to about 20 volume percent based on the volume of the embolic composition. Alternatively, the amount of radiopacifier can be determined based on the relative volume of the solid-aggregate material, which comprises from about 5% to about 40%, by volume of the liquid composition. Preferably, the radiopacifier is present in an amount of from about 25% to about 100%, by volume of the solid-aggregate material. More preferably, the radiopacifier is present in an amount of from about 60% to about 100%, by volume of the solid-aggregate material.

The composition of the invention can be provided as individual components or as mixtures of the individual components wherein the alkyl cyanoacrylate monomer and the stabilizing component are combined and wherein the solid-aggregate material and the plasticizer also are integrated. The rheology modifying polymer can be added to a mixture containing the monomer and/or a mixture containing the plasticizer. When the composition is provided as a single composition, the plasticizer and the solid-aggregate material are mixed before contacting the solid-aggregate material with the alkyl cyanoacrylate monomer.

Therefore, as previously described herein, the composition of the invention can comprise a matrix-forming component and optionally a solid-aggregate material, wherein the matrix-forming component comprises liquid cyanoacrylate monomers and at least a stabilizer and a plasticizer. The solid-aggregate material comprises a radiopacifier, and the rheology modifying agent is incorporated into the composition either as a matrix-forming component, as a solid-aggregate material, or as a separate component altogether.

Typically, the matrix-forming component of the composition comprises from about 60% to about 94%, by volume of the embolic composition. The solid-aggregate material comprises from about 5% to about 40%, by volume of the embolic composition. Preferred and more preferred compositions of the invention are provided in the table below:

| Preferred and More Preferred Compositions with Rheological Modifying Agent[1] | | | | | |
|---|---|---|---|---|---|
| Matrix-Forming Component[2] | | | Solid-Aggregate Material | | |
| Ingredient | Prefer (w/w %) | More Prefer (w/w %) | Ingredient | Prefer (v/v %) | More Prefer (v/v %) |
| monomer[3] | 20-75 | 30-70 | radiopacifier | 25-100 | 60-100 |
| plasticizer | 10-75 | 30-60 | particulate rheology modifying agent | 0-75 | 0-40 |
| polymer rheology modifying agent | 0-10 | 1-5 | | | |

[1]w/w % represents "by weight" percent relative to the matrix-forming components; v/v % represents "by volume" percent relative to the solid-aggregate material
[2]A stabilizer also is included in minimal amounts of parts per million range and, therefore, is not represented in the table.
[3]"Monomer" refers to an alkyl cyanoacrylate monomer.

The composition of the present invention can be administered with any suitable method. Typically, the components of the composition are provided either separately or in combination as previously described. The components of the composition are mixed together to form the embolic composition, which can be delivered by any suitable method. Suitable methods for administering the composition will deliver the liquid injectable composition preferably directly to the delivery site or the location of the diseased, damaged, or otherwise compromised vasculature or tissue. Upon contact with an ionic environment of the delivery site, for example blood, the composition will form a solidified composition, or embolic block.

Typically, the composition of the invention is delivered in a catheter device that is prefilled with a nonionic solution, for example, a 5% dextrose solution. Commercially available methods can include needles, catheter devices, or stereotaxic placement devices, preferably in conjunction with an imaging technology that provides the practitioner with guidance as to the placement of the composition. Some devices and methods already known to those of skill in the art include, for example, in U.S. Pat. No. 5,925,683, which discloses a method for introducing liquid embolic agents/solutions into the human body to form precipitated embolic occlusion masses; U.S. Pat. No. 5,702,361, which describes a method of embolizing a vascular site in a patient's blood vessels comprising introducing via a catheter a non-particulate agent at the vasculature site; and U.S. Pat. No. 5,882,334, which describes a catheter assembly for delivering embolic compositions.

The compositions can be used advantageously in conjunction with any method that employs an embolizing agent, occluding agent, bulking agent, or such composition that creates an embolic block, occlusion, or increase in tissue volume. More particularly, the embolic agent selectively creates a blockage in the lumen of a blood vessel, duct, fistula, or other like body passages. A preferred method for delivering the embolic agent would involve delivering the liquid embolic composition via a microcatheter into the vascular region to be embolized.

In the case of aneurysm treatment, placement of a secondary embolic containment device, either temporarily or permanently, is preferred. Temporary aneurysmal neck occlusion devices can be achieved, for example, using a balloon catheter placed in a position such that the aneurysm neck is sufficiently occluded as to allow the catheter to be inserted into the aneurysm and to prevent the escape of any of the embolic composition. Permanent implantable devices also can be used to prevent escape of the embolic composition, for example, a stent or a neck-bridging device, such as the TRI-SPAN COIL™ intracranial aneurysm device (Target Therapeutics, Inc., Fremont, Calif., U.S.A.) or any other device intended to prevent the migration of embolic materials or embolic constructs out of the aneurysm. The material also can be delivered using devices intended to both deliver and contain embolic materials, such as the device described in U.S. Pat. No. 5,795,331.

The composition has the desired viscosity and cohesive characteristics to administer into an ionic fluid environment, such as blood. The composition forms a solid structure upon contact with the ionic environment. In addition, the present invention is radiopaque which allows for observation by a practitioner with x-ray or other like or equivalent imaging techniques. The composition and method of the present invention can be advantageously used to block blood flow to certain tissues, areas, or cavities in the vasculature. Such treatment can be used to alleviate symptoms experienced because of AVM, for example, bleeding, seizures, or cerebral or other hemorrhage. The method can stabilize or mitigate rupture of an aneurysm when properly employed.

Although the present invention has been described with reference to a preferred embodiment, those skilled in the art will recognize that changes can be made in form and detail without departing from the spirit and scope of the present invention. As such, it is intended that the detailed description is regarded as illustrative rather than limiting and the invention is defined by the appended claims.

What is claimed is:

1. A medical composition comprising:
a matrix-forming component comprising alkyl cyanoacrylate monomers, a stabilizer, and a plasticizer;
a solid aggregate material comprising a radiopacifier; and
a polymeric non-cyanoacrylate rheology modifying agent that has an average molecular weight greater than 200,000, wherein the non-cyanoacrylate rheology modifying agent is a polymeric compound selected from the group consisting of poly(acrylates), poly(alkenes), poly(alkyl oxides), poly(amides), poly(carbonates), cellulosic polymers and copolymers, poly(dienes), poly(esters), poly(methacrylates), poly(saccharides), poly(siloxanes), poly(styrenes), poly(urethanes), poly(vinyl ethers), iodinated polymers and copolymers thereof, and mixtures thereof.

2. The composition of claim 1, the solid aggregate material further comprising a second non-cyanoacrylate rheology modifying agent comprising an inorganic particulate material.

3. The composition of claim 1, wherein the non-cyanoacrylate rheology modifying agent is soluble in the alkyl cyanoacrylate monomers or in the plasticizer.

4. The composition of claim 1, wherein the non-cyanoacrylate rheology modifying agent and the plasticizer is the same material.

5. The composition of claim 1, wherein the non-cyanoacrylate rheology modifying agent comprises from greater than 0% to about 10%, by weight of the matrix-forming components.

6. The composition of claim 1, wherein the non-cyanoacrylate rheology modifying agent comprises from about 1% to about 5%, by weight of the matrix-forming components.

7. The composition of claim 1, wherein the alkyl cyanoacrylate monomer is a compound of the formula $H_2C=C(CN)-C(O)OR$, wherein R is an alkyl group of about 1 to about 18 carbons.

8. The composition of claim 7, wherein the group represented by R is an alkyl group of about 4 to about 10 carbons.

9. The composition of claim 1, wherein the alkyl cyanoacrylate monomer is present in an amount of from about 20% to about 75%, by weight of the matrix-forming component.

10. The composition of claim 1, wherein the alkyl cyanoacrylate monomer is present in an amount of from about 30% to about 70%, by weight of the matrix-forming component.

11. The composition of claim 1, wherein the stabilizer is an inorganic acid, an organic acid, a free radical inhibitor, an antioxidant, or a mixture thereof.

12. The composition of claim 1, wherein the stabilizer is present in an amount of from about 50 ppm to about 500 ppm.

13. The composition of claim 1, wherein the radiopacifier is selected from the group consisting of Ta, TaO, Au, Pt, Zr, ZrO, bismuth subcarbonate, and barium sulfate.

14. The composition of claim 1, wherein the radiopacifier comprises radio-opaque particles with surface-modifying molecules adsorbed to or bonded to the surfaces of said particles for improving the stability of a suspension of said particles within said composition.

15. The composition of claim 1, wherein the radiopacifier is about 25% to about 100%, by volume of the solid-aggregate material.

16. The composition of claim 1, wherein the radiopacifier is about 60% to about 100%, by volume of the solid-aggregate material.

17. The composition of claim 1, wherein the plasticizer is selected from the group consisting of organic esters containing 10 or more carbon atoms and polymeric compounds having a glass transition temperature less than 20° C.

18. The composition of claim 1, wherein the plasticizer is selected from the group consisting of aromatic esters, alkyl esters, phthalate esters, citrate esters, glycerol esters, plant derived oils, animal derived oils, silicone oils, iodinated oils, vitamins A, C, E, and acetates and esters thereof, and mixtures thereof.

19. The composition of claim 1, wherein the plasticizer is about 10% to about 75%, by weight of the matrix-forming component.

20. The composition of claim 1, wherein the plasticizer is about 30% to about 60%, by weight of the matrix-forming component.

21. The composition of claim 2, wherein the inorganic particulate material is selected from the group consisting of fumed silica, silicatious earth, bentonite, and mixtures thereof.

22. The composition of claim 2, wherein the second non-cyanoacrylate rheology modifying agent is a particulate material comprising from greater than 0% to about 75%, by volume of the solid-aggregate materials.

23. The composition of claim 2, wherein the second non-cyanoacrylate rheology modifying agent is a particulate material comprising from greater than 0% to about 40%, by volume of the solid-aggregate materials.

24. The composition of claim 2, wherein the second non-cyanoacrylate rheology modifying agent comprises inorganic particles with surface-modifying molecules adsorbed to or bonded to the surfaces of said particles for improving the stability of a suspension of said particles within said composition.

* * * * *

UNITED STATES PATENT AND TRADEMARK OFFICE
CERTIFICATE OF CORRECTION

PATENT NO. : 7,687,053 B2  Page 1 of 1
APPLICATION NO. : 09/933316
DATED : March 30, 2010
INVENTOR(S) : Porter It is certified that error appears in the above-identified patent and that said Letters Patent is hereby corrected as shown below:

Specification, Col. 5, line 33, after "of", change "pone" to -- one --.

Specification, Col. 6, line 13, before "known", change "are-already" to -- are already --.

Specification, Col. 8, line 6, after "alters the", change "Theological" to -- rheological --.

Signed and Sealed this

Eleventh Day of May, 2010

David J. Kappos
*Director of the United States Patent and Trademark Office*